US008628326B2

(12) United States Patent
Rubio Cebriá

(10) Patent No.: US 8,628,326 B2
(45) Date of Patent: Jan. 14, 2014

(54) DENTAL PROSTHESIS

(75) Inventor: Justo Manuel Rubio Cebriá, Valencia (ES)

(73) Assignee: Justo Manuel Rubio Cebria, S.L., Valencia (ES)

(*) Notice: Subject to any disclaimer, the term of this patent is extended or adjusted under 35 U.S.C. 154(b) by 0 days.

(21) Appl. No.: 13/007,253

(22) Filed: Jan. 14, 2011

(65) Prior Publication Data

US 2011/0177476 A1  Jul. 21, 2011

(30) Foreign Application Priority Data

Jan. 15, 2010  (ES) .................................. 201030033

(51) Int. Cl.
*A61C 13/10* (2006.01)

(52) U.S. Cl.
USPC .......................................................... 433/194

(58) Field of Classification Search
USPC ................. 433/172–179, 191–193; 264/18
See application file for complete search history.

(56) References Cited

U.S. PATENT DOCUMENTS

| | | | | |
|---|---|---|---|---|
| 4,184,252 A * | 1/1980 | Krol et al. | ...................... | 433/172 |
| 4,225,668 A * | 9/1980 | Bartoli | .......................... | 433/176 |
| 4,767,328 A * | 8/1988 | Branemark | ................ | 433/168.1 |
| 4,784,608 A * | 11/1988 | Mays | ............................. | 433/172 |
| 5,286,191 A * | 2/1994 | Poveromo | ....................... | 433/74 |
| 6,116,070 A * | 9/2000 | Oshida et al. | ..................... | 72/60 |
| 7,214,061 B2 * | 5/2007 | Fortin | ........................... | 433/173 |
| 2002/0102517 A1 * | 8/2002 | Poirier | ......................... | 433/173 |
| 2002/0192620 A1 * | 12/2002 | Jorneus et al. | ................ | 433/173 |
| 2003/0108845 A1 * | 6/2003 | Giovannone et al. | ......... | 433/173 |
| 2004/0038181 A1 * | 2/2004 | Fortin | ........................... | 433/173 |
| 2004/0166476 A1 * | 8/2004 | Weissman | ..................... | 433/173 |
| 2006/0223029 A1 * | 10/2006 | Berger | .......................... | 433/172 |
| 2007/0281283 A1 * | 12/2007 | Lundgren | ..................... | 433/214 |

* cited by examiner

*Primary Examiner* — Cris L Rodriguez
*Assistant Examiner* — Mirayda A Aponte
(74) *Attorney, Agent, or Firm* — Merchant & Gould P.C.

(57) ABSTRACT

Dental prosthesis to be fixed on implants (103) is arranged in a dental arch (100), completely or partially edentulous. The prosthesis (1) includes a primary structure (200) which is configured to be screwed on the implants (103) of the dental arch (100) and which has primary inserts (410, 420, 430, 440); and a secondary structure (300) which is configured to support a reproduction (104) of the teeth and of the gum of the dental arch (100) and which has secondary inserts (510, 520, 530, 540). The primary inserts (410, 420, 430, 440) and the secondary inserts (510, 520, 530, 540) are configured to work in collaboration and allow the coupling of the secondary structure (300) on the primary structure (200) through a vestibular insertion.

13 Claims, 7 Drawing Sheets

DENTAL PROSTHESIS

This application claims benefit of Ser. No. 201030033, filed 15 Jan. 2010 in Spain and which application is incorporated herein by reference. To the extent appropriate, a claim of priority is made to the above disclosed application.

OBJECT OF THE INVENTION

The present invention refers to a dental prosthesis of the type which are fixed on a plurality of implants arranged in a dental arch, completely or partially edentulous, corresponding to a patient's maxilla or mandible. Specially, for completely toothless patients or those who have a reduced number of teeth (natural or prosthetic).

The dental prosthesis of the present invention has been specially designed to be easily mounted and dismounted in the patients mouth by a vestibular insertion, equivalent to a horizontal insertion. Similarly, the dental prosthesis of the present invention depends much less on the good or bad implant placement compared with existing prosthesis and it also presents an aesthetic finish.

BACKGROUND OF THE INVENTION

Nowadays, the mounting and dismounting of any dental prosthesis of the aforementioned type is performed exclusively by an axial insertion, that is, through a vertical insertion.

There are numerous situations in which implants of the dental arch are in unfavourable conditions, such as due to excess inclination, for being out of the natural space of the tooth or for not being subgingival (deep under the gum), among others. All these situations are not only highly problematic for the patient, who suffer all the discomfort without getting the desired aesthetic results, but they are also notably detrimental to dentists and dental technicians. In this sense, screwed and cemented prostheses are a clear example of these inconveniences.

As regards screwed prostheses, they have the advantage that they can be removed at any time by simply loosening the screws that keep them fixed to the implants, to which they are mounted and dismounted by axial insertions. However, the elaboration of this type of prostheses is quite complex, presents multiple adjustment difficulties and even aesthetic problems. The chimneys used to do the holes through dental pieces to allow screw access to the implants are greatly responsible for this. For example, any small variation in the final position of the chimney in the prosthesis with respect to its original position in the mouth can cause serious adjustment problems. It is also frequent that the holes drilled by chimneys are in highly visible areas of the dental piece, due to a faulty placement of implants, which results in undesired aesthetic results. Another very important aspect is the possibility of chimneys being located in highly occluded areas (cuspids o pits), which produces failures in the prosthesis function.

As regards cemented prostheses, these are also mounted and dismounted by axial insertions, yet they do not have as many elaboration and mounting inconveniences as screwed prostheses since they do not use chimneys. In this case, the joining with the implants is performed through stumps, which are actually mechanical connections, between a first piece screwed to the implant and a second piece located in the prosthesis. In spite of the apparent simplicity of this type of prosthesis, its elaboration and mounting still produces some of the aforementioned problems. Particularly, wrong implant placement can cause important inconveniences such as, for example difficulties placing the first pieces which can seriously hinder the fitting with second pieces placed in the prostheses. It may also be the case that there exist small variations in the final position of the second pieces on the prosthesis in relation with their original position in the mouth, which causes serious adjustment problems.

The present invention solves the aforementioned problems in a highly satisfactory manner thanks to an easily mounted and dismounted dental prosthesis of vestibular insertion, much less dependent on the right or wrong implant placement, with a highly aesthetic finish and which does not exclude any of the advantages and features of the previous prostheses.

SUMMARY OF THE INVENTION

In order to solve the aforementioned problems, the dental prosthesis of the present invention is of the type that is fixed on a plurality of implants arranged in a completely or partially edentulous dental arch. Such prosthesis comprises:
  a primary structure configured to be screwed over the implants of the dental arch and which has primary insertion means; and
  a secondary structure configured to support a reproduction of the teeth and of the gum of the dental arch and which has secondary insertion means.

Also, the primary insertion means and the secondary insertion means are configured to work collaboratively and allow the coupling of the secondary structure on the primary structure by a vestibular insertion. Vestibular refers to the outer side of teeth, that is to say the one seen when someone smiles. Vestibular insertion is equivalent to a horizontal insertion.

The primary structure comprises:
  a frontal wall configured to use a front space, totally or partially, corresponding to the location of incisors and canines of the dental arch; and
  at least one lateral wall connected with the frontal wall which is configured to occupy a lateral space, partially or totally, corresponding to the location of molars and premolars of one of the dental arch sides.

Preferably, the frontal wall has a conic shape which is closed towards the dental arch and which is very helpful for orienting and facilitating its fixing to the implants, while the lateral wall is placed in a perpendicular position with respect to an occlusal plane. The term "occlusal" refers to the masticatory surface of molars and premolars. The frontal wall shape and the lateral wall shape follow the lingual or palatine morphology whether it is the lower or upper arch respectively, so as to provide a better adjustment. The frontal and lateral walls comprise, each of them, at least one fixing pillar oriented so as to facilitate the fixing of the implants. Each of these fixing pillars comprises:
  one end coinciding with one of the implants of the dental arch and which is configured to fit with such implant; and
  a through hole which is configured to receive a fixation screw which is connected with the implant.

Also, the secondary structure comprises:
  a frontal covering wall configured to attach with the outer face of frontal wall of primary structure and cover it; and
  at least one lateral covering wall attached to the frontal covering wall, configured to fit with the outer face of the lateral wall of primary structure and cover it.

The formation of said walls is adjusted to avoid cracks and holes between the primary and secondary structures, and thus, leftover food accumulation zones or zones where air can be accumulated are also avoided.

Preferably, the frontal covering wall and the lateral covering wall comprise a plurality of protuberances configured to withstand the reproduction of dental pieces and gum of the dental arch and to facilitate its formation. Such reproduction can be performed by means of any existing techniques or a combination thereof, including sinterization and mechanization by means of computer-aided design and computer-aided manufacturing (CAD-CAM). These protuberances will be adapted to the applied technique, as well as the convenience of its use.

The prosthesis of the present invention offers a solution to a certain number of different rehabilitations, although one of the most suitable ones is the one that solves the issue of patients with one or both totally edentulous dental arches. In these cases, the prosthesis covers the whole toothless dental arch, be it the upper or lower one, so its primary structure has a frontal wall joined to two lateral walls, while its secondary structure has a frontal covering wall joined to two lateral covering walls.

However, there can be other situations where the primary and secondary structures have a different configuration. For example, a patient who has all their molars and premolars in one side of the dental arch, or even some canine or incisors next to them, whether they be natural dental pieces or screwed prostheses. In this case a frontal wall is configured so as to partially occupy the space of incisors and canines of the dental arch, joined to only one lateral wall which partially occupies the space of molars and premolars. The secondary structure is configured following the same guidelines in order to obtain a hybrid prosthesis.

Thus, there exists a certain number of cases which allow the use of hybrid prostheses applying the same aforementioned principles of configuring the frontal and lateral walls to occupy the space of dental pieces missing in the dental arch, to comply with basic above defined requirements of the primary structure. Another example can be a patient who still has the third and second canines in both sides of the dental arch.

The primary and secondary insertion means comprise respectively primary support means and secondary support means which allow the occlusal support of the secondary structure over the primary structure. That is to say, a perpendicular or axial support with respect to the molars and premolars masticatory surface. Preferably, the primary and secondary support means comprise respectively an occlusal external flat surface on the primary structure and an internal flat occlusal surface on the secondary structure. In this way, the secondary structure support over the primary structure is an absolutely flat support which helps distribute axial forces and represents an insertion guiding plane during vestibular insertion as it will be seen hereinafter.

Additionally, the primary insertion means and secondary insertion means respectively comprise primary guiding means and secondary guiding means configured to guide the secondary structure over the primary structure during the vestibular insertion. Preferably, the primary guiding means comprise a plurality of horizontal recesses or protrusions mechanized in a staggered manner along the outer face of the lateral wall. While the secondary insertion means comprise a plurality of horizontal protrusions or recesses mechanized along the inner face of the lateral covering wall, configured to fit with the horizontal recesses or protrusions respectively of the primary guiding means, and slide along them until the secondary structure is completely supported over primary structure. The terms "horizontal" mentioned in the present paragraph are also equivalent to "parallel to the occlusal plane". Preferably, recesses are located in the primary structure, while protrusions are located in the secondary structure, although they can be distributed in the opposite way. Recesses can be obtained by milling in the form of staggered rails on the corresponding face, while the protrusions can be obtained by adding material on the corresponding face to create a particular thickness or volume with complementary dimensions thereto. Besides facilitating the guidance during the vestibular insertion, the primary guiding means and secondary guiding means also counteract axial and non-axial stress.

Additionally, the primary insertion means and the secondary insertion means respectively comprise primary fitting means and secondary fitting means configured to assemble the secondary structure with the primary structure during the vestibular insertion. Preferably, the primary fitting means comprise a plurality of marks or horizontal reliefs mechanized with a half-moon shape on the outer occlusal face of the frontal wall. While the secondary fitting means comprise a plurality of marks or horizontal reliefs mechanized on the occlusal inner face of the frontal covering wall, configured to fit with the marks or horizontal reliefs of the primary fitting means respectively. The terms "horizontal" mentioned in the present paragraph are also equivalent to "parallel to the occlusal plane". Preferably, the marks are located in the primary structure, while the reliefs are located in the secondary structure, although they can be distributed in the opposite way. The marks can be obtained by milling with a half-moon shape on the corresponding face, while the protrusions can be obtained by adding material on the corresponding face to create a particular thickness or volume with complementary dimensions thereto. Besides facilitating the assembling during the vestibular insertion, the primary fitting means and the secondary fitting means also counteract axial and non-axial stress.

According to a second preferred embodiment, the primary fitting means comprise a rail-like front extension of the frontal wall upper part. While the secondary fitting means comprise a fastening notch mechanized over the inner occlusal face of the frontal covering wall configured to fit with the primary fitting means front extension.

Both embodiments of the primary and secondary fitting means described above offer different uses. In this sense, the first embodiment of the fitting means is ideal for class II occlusion compensations. Specifically, thanks to the "platform-type" design they have, the incisor position of the corresponding secondary structure can be moved backwards to the maxilla arch, even behind the location of the implants, until reaching the desired aesthetic degree. Also, the second embodiment of the fitting means is ideal for class III occlusion compensation. Specifically, thanks to the "claw-type" design that they have, the incisor position of the corresponding secondary structure can be moved forward to the arch of the maxilla, even behind the location of the implants, until reaching the desired aesthetic degree. Also, the second embodiment of the fitting means is ideal for class III occlusion compensation. Specifically, thanks to the "claw-type" design that they have, the incisor position of the secondary structure corresponding to the maxilla arch can be moved forward, until reaching the desired aesthetic degree.

Additionally, the primary insertion means and the secondary insertion means respectively comprise primary retention means and secondary retention means configured to fix the secondary structure on the primary structure after the vestibular insertion. Having a primary structure fixed on the implants, regardless of the secondary structure, enables to adopt working modes which greatly simplify the dentist's o dental technician's work and they increase patients comfort. For example, in case of having to fix any definitive prosthesis, said prosthesis can be easily replaced by a provisional prosthesis, since it is only necessary to release the secondary structure from the primary structure, which is permanently attached to the implants. The primary retention means and the secondary retention means are also designed to facilitate these tasks. In this sense, we contemplate different solutions that can be used independently or jointly.

In the first solution, the primary retention means and the secondary retention means comprise a plurality of lateral orifices respectively located on the lateral wall and on the lateral covering wall, suitable for the use of retention pins. Even though screws can also be used, retention pins have the advantage of faster mounting and dismounting.

According to a second solution, the primary retention means and the secondary retention means comprise a plurality of axial orifices respectively located on the primary external occlusal surface and on the secondary internal occlusal surface, suitable for the use of retention screws.

According to a third solution, the primary retention means comprise a primary end orifice placed at the end of the recess or horizontal protrusion furthest from the frontal wall. While the secondary retention means comprise an axis arranged at the end of the recess or horizontal protrusion furthest from the frontal wall, which fits with the primary end orifice. Said primary end orifice can have any needed geometric configuration such as circular, square, triangular, among others, according to the axis geometric configuration.

According to a fourth solution, the primary retention means comprise a primary fitting orifice located in at least one of the marks or reliefs of the frontal wall. While the secondary retention means comprise a secondary fitting orifice located in at least one of the reliefs or marks of the frontal covering wall coinciding with the primary fitting orifice suitable for the use of fitting screws.

The present invention can be manufactured with any of the most widely used materials in this sector such as, Ti, Cr—Ni, Cr—Co, Au, Pd, Zi, among others.

BRIEF DESCRIPTION OF THE DRAWINGS

The following is a brief description of a series of drawings which help understand the invention better relating to two embodiments of said invention which are presented as a non-limiting examples thereof.

DETAILED DESCRIPTION OF THE PREFERRED EMBODIMENT(S)

Figure 1:
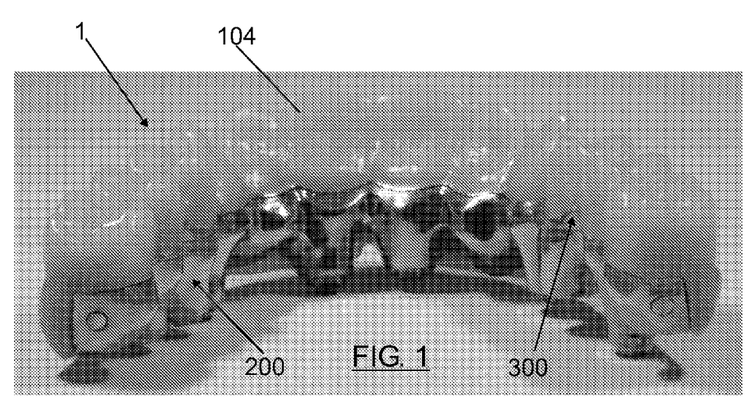
FIG. 1 is a perspective view of the prosthesis of the present invention.
Figure 2A:
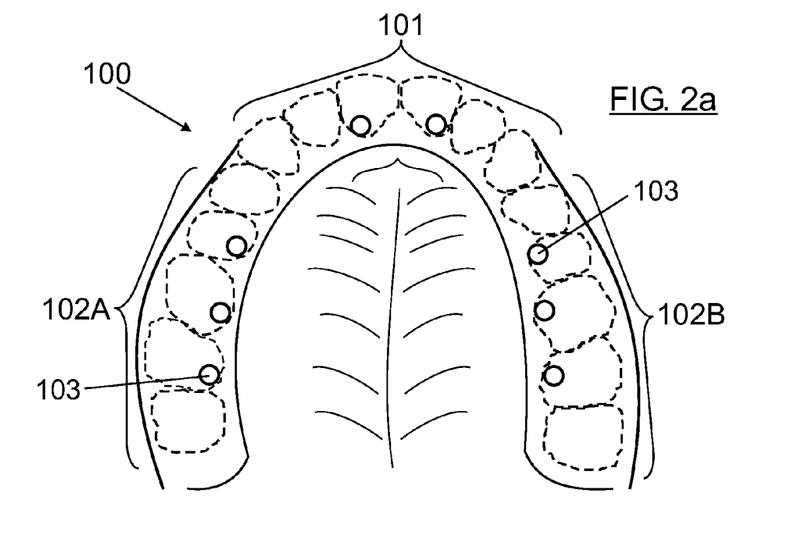
FIG. 2a is a schematic representation of the dental arch corresponding to the maxilla.
Figure 2B:
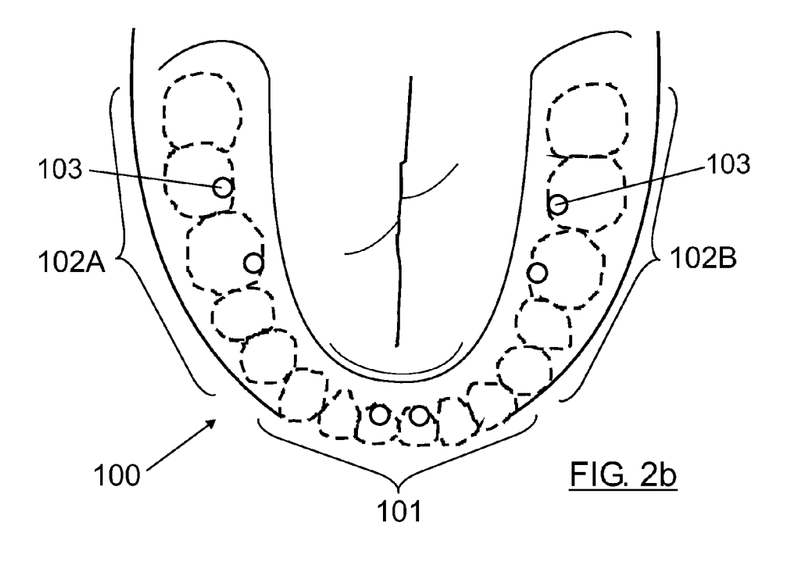
FIG. 2b is a schematic representation of the dental arch corresponding to the mandible.

FIG. 1 shows a dental prosthesis (1) according to the present invention. As it can be seen, this prosthesis (1) is of the type that are fixed on a plurality of implants (103) arranged in a dental arch (100), as the ones shown in FIGS. 2a and 2b. Said prosthesis (1) comprises:
 a primary structure (200) which is configured to be screwed on the implants (103) of the dental arch (100) and which has primary insertion means (410, 420, 430, 440); and
 a secondary structure (300) which is configured to support a reproduction (104) of the teeth and of the gum of the dental arch (100) and which has secondary insertion means (510, 520, 530, 540).

Also, the primary insertion means (410, 420, 430, 440) and the secondary insertion means (510, 520, 530, 540) are configured to work in collaboration and allow the coupling of the secondary structure (300) on the primary structure (200) through a vestibular insertion.

The prosthesis (1) of the present example is intended for a patient who has a completely edentulous dental arch (100), although as it was mentioned before the dental prosthesis (1) of the present invention enables to solve a certain number of different rehabilitations.

Figure 3:
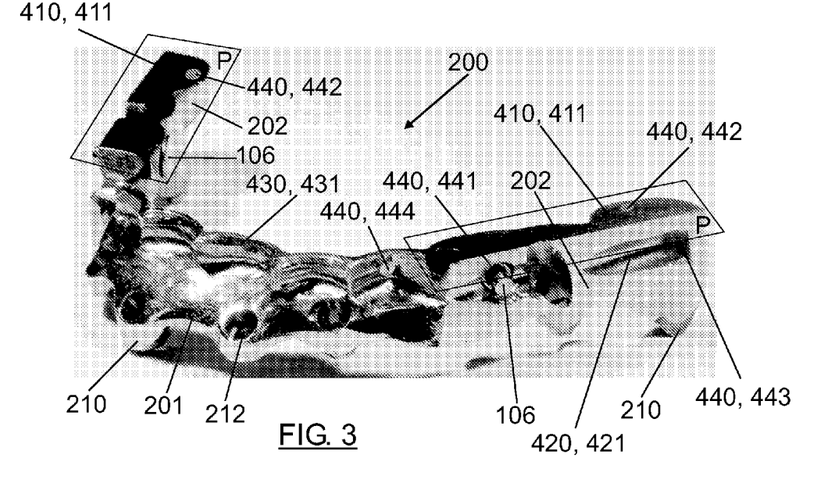
FIG. 3 is a perspective view of the upper part of the primary structure according to a first embodiment.

FIG. 3 shows the primary structure (200) comprising:
 a frontal wall (201) which is configured to occupy a frontal space (101), partially or totally, corresponding to the location of the incisors and canines of the dental arch (100); and
 at least one lateral wall (202) joined to the frontal wall (201) which is configured to occupy the lateral space (102A, 102B), partially or totally, corresponding to the location of the molars and premolars of one of the sides of the dental arch (100).

As it can be seen, the frontal wall (201) has a conic shape which is closed towards the dental arch (100) and which is very helpful to orient and facilitate its fixing to the implants (103), while the lateral wall (202) is arranged perpendicularly to an occlusal plane (P). The shape of the frontal wall (201) and of the lateral wall (202) also has the morphology of the lingual or palate part, according to whether it is the lower or upper arch respectively, to provide a better fit. The frontal (201) and lateral (202) walls comprise each one of them at least a fixing pillar (210) oriented to facilitate the fixing to the implants (103).

Figure 4:
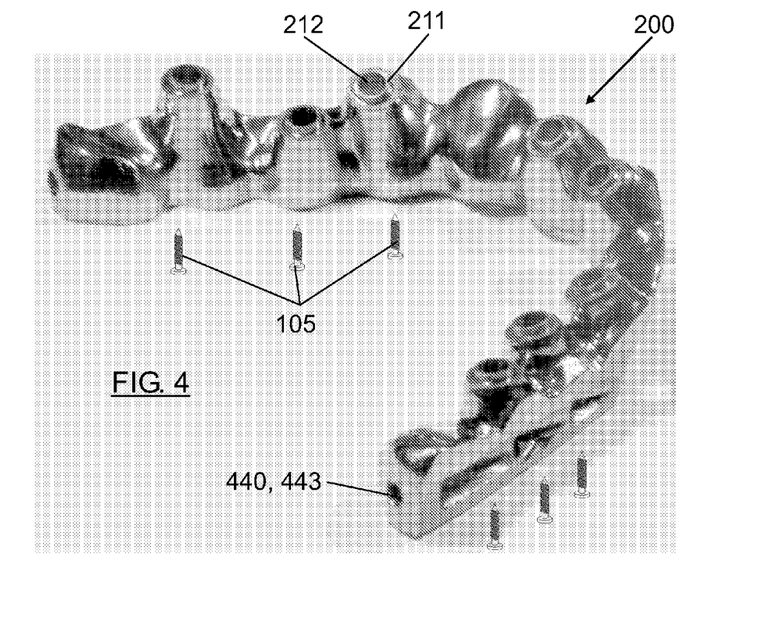
FIG. 4 is a perspective view of the lower part of the primary structure according to a first embodiment.

FIG. 4 shows that each one of the fixing pillars (210) has:
 an end (211) coinciding with one of the implants (103) of the dental arch (100) and which is configured to fit with said implant (103); and
 a through hole (212) which is configured to receive a fixation screw (105) which connects with the implant (103).

Figure 5:
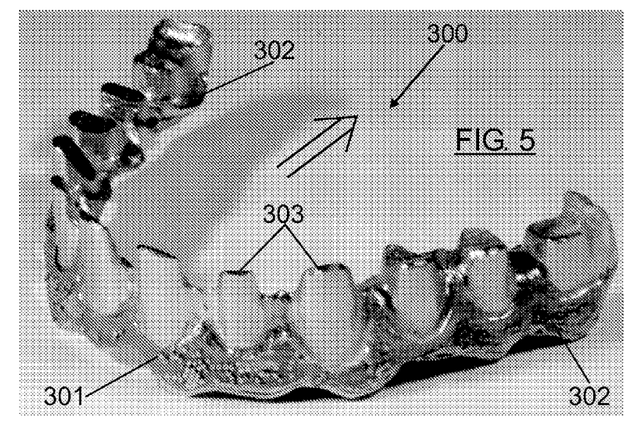
FIG. 5 is a perspective view of the upper part of the secondary structure according to a first embodiment.

FIG. 5 shows that the secondary structure (300) comprises:
 a frontal covering wall (301) constituted to fit with the outer face of the frontal wall (201) and cover it; and
 at least one lateral covering wall (302) attached to the frontal covering wall (301) formed to fit with the outer face of the lateral wall (202) and cover it.

As it can be seen, the frontal covering wall (301) and the lateral covering wall (302) comprise a plurality of protuberances (303) configured to support the reproduction (104) of the teeth and of the gum of the dental arch (100) and facilitate its formation.

For illustration purposes, FIG. 5 includes an arrow showing the direction of the vestibular insertion by means of which the coupling of the secondary structure (300) on the primary structure (200) is performed.

Figure 6:
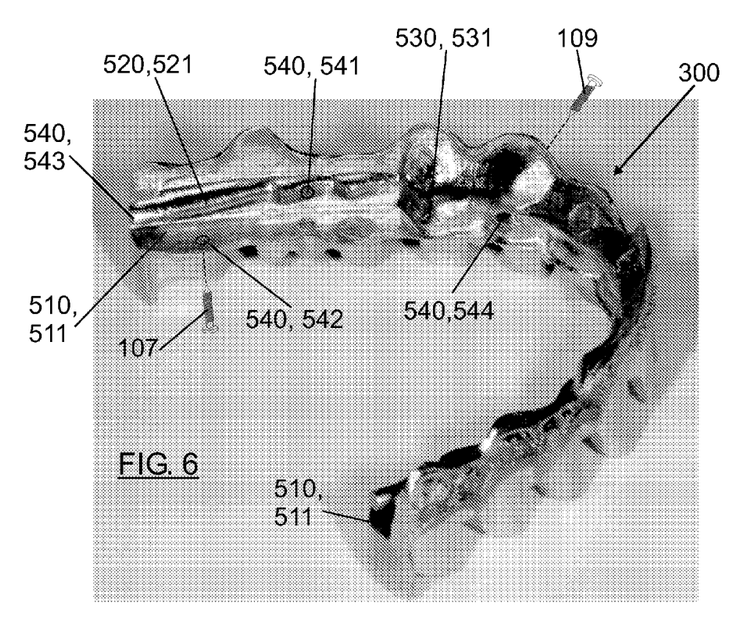
FIG. 6 is a perspective view of the lower part of the secondary structure according to a first embodiment.
Figure 7:
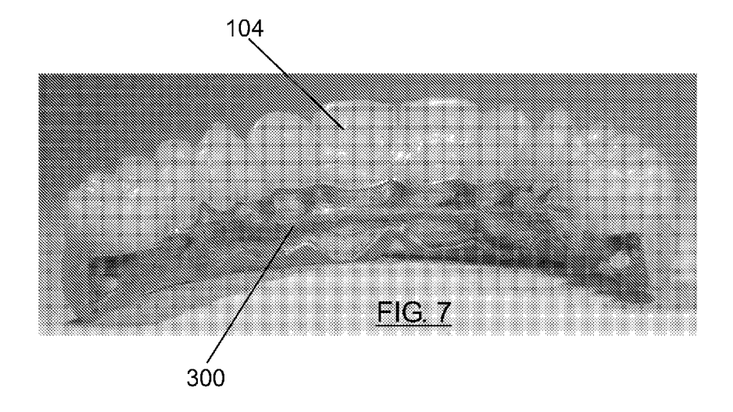
FIG. 7 is a perspective view of the rear part of the secondary structure together with the reproduction of the teeth and of the gum according to a first embodiment.
Figure 8:
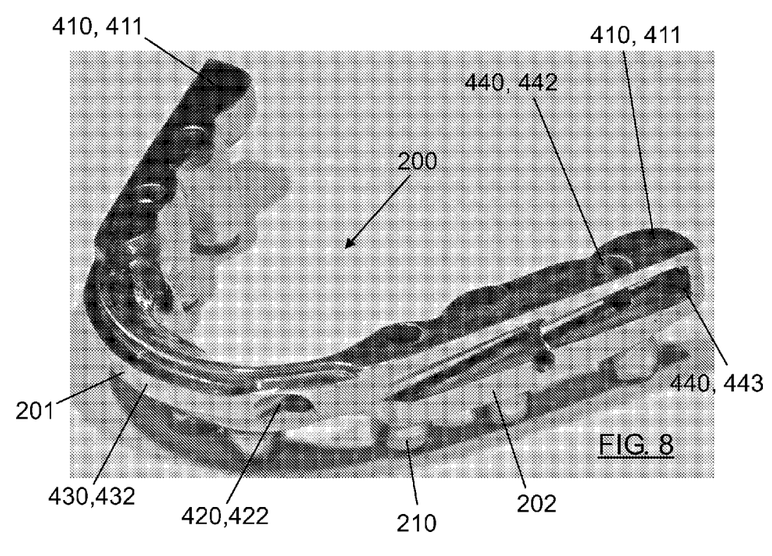
FIG. 8 is a perspective view of the upper part of the primary structure according to a second embodiment.

The primary insertion means (410, 420, 440) and the secondary insertion means (510, 520, 530, 540) respectively comprise primary support means (410) shown in FIG. 8 and secondary support means (510) shown in FIG. 6 which allow the occlusal support of the secondary structure (300) on the primary structure (200). As it can be seen in FIGS. 3 and 6, the primary support means (410) and the secondary support means (510) comprise respectively, an external flat occlusal surface (411) on the primary structure (200) and an internal flat occlusal surface (511) on the secondary structure (300). As it can be seen, both surfaces (411, 511) are arranged on the occlusal plane (P). In this way, the support of the secondary structure (300) on the primary structure (200) is a completely flat support, which helps distribute the axial forces and which represents an insertion guiding plane during vestibular insertion.

Additionally, the primary insertion means (410, 420, 430, 440) and the secondary insertion means (510, 520, 530, 540) comprise respectively primary guiding means (420) and secondary guiding means (520) configured to guide the secondary structure (300) on the primary structure (200) during the vestibular insertion. As it can be seen in FIGS. 3 and 6, the primary guiding means (420) comprise a plurality of horizontal recesses (421) mechanized in a staggered manner along the outer face of the lateral wall (202). While the secondary guiding means (520) comprise a plurality of horizontal protrusions (521) mechanized along the inner face of the lateral covering wall (302) constituted to fit with the horizontal recesses (421) of the primary guiding means (420) and move along them until the secondary structure (300) rests completely on the primary structure (200). Besides facilitating the guiding during the vestibular insertion, the primary guiding means (420) and the secondary guiding means (520) also have the function of counteracting axial and non-axial stress. Finally, as it can be seen, the use of the term horizontal is equivalent to parallel to the occlusal plane (P).

Although it is not shown in the present example, as it was indicated before, the use of recesses (421) and protrusions (521) can be inverted, thus having protrusions (421') in the primary structure (200) and recesses (521') in the secondary structure (300) fulfilling the same function.

Additionally, the primary insertion means (410, 420, 430, 440) and the secondary insertion means (510, 520, 530, 540) also comprise respectively primary fitting means (430) and secondary fitting means (530) configured to assemble the secondary structure (300) with the primary structure (200) during the vestibular insertion. As it can be seen in FIGS. 3 and 6, the primary fitting means (430) comprise a plurality of horizontal marks (431) mechanized with a half-moon shape on the outer occlusal face of the frontal wall (201). While the secondary fitting means (530) comprise a plurality of horizontal reliefs (531) mechanized on the inner occlusal face of the frontal covering wall (301) formed to fit respectively with the horizontal marks (431) of the primary fitting means (430). Besides facilitating the assembly during the vestibular insertion, the primary fitting means (430) and the secondary fitting means (530) also have the function of counteracting both axial and non-axial stress. Finally, as it can be seen, the use of the term horizontal is equivalent to parallel to the occlusal plane (P).

Although it is not shown in the present example, as it was indicated before, the use of marks (431) and reliefs (531) can be inverted, thus having reliefs (431') in the primary structure (200) and marks (531') in the secondary structure (300) fulfilling the same function.

Additionally, the primary insertion means (410, 420, 430, 440) and the secondary insertion means (510, 520, 530, 540) also comprise respectively primary retention means (440) and secondary retention means (540) configured to fix the secondary structure (300) on the primary structure (200) after the vestibular insertion. The primary retention means (440) and the secondary retention means (540) offer different solutions which can be used independently or jointly, as shown in the present example.

In the first one of them, the primary retention means (440) and the secondary retention means (540) comprise a plurality of lateral orifices (441, 541) arranged respectively in a way coincidental on the lateral wall (202) and on the lateral covering wall (302) suitable for the use of retention pins (106).

According to a second solution, the secondary retention means (540) comprise a plurality of axial orifices (442, 542) arranged respectively in a way coincidental on the primary outer occlusal surface (411) and on the secondary inner occlusal surface (511) suitable for the use of retention screws (107).

According to a third solution, the primary retention means (440) comprise a primary end orifice (443) arranged at the end of the horizontal recess (421) furthest from the frontal wall (201). While the secondary retention means (540) comprise an axis (543) arranged at the end of the horizontal protrusion (521) furthest from the frontal wall (201) which fits with the primary end orifice (443).

Although it is not shown in the present example, if the position of the recesses (421) and protrusions (521) is inverted, the axis (523) is arranged on the recess (521').

According to a fourth solution, the primary retention means (440) comprise a primary fitting orifice (444) arranged in at least one of the marks (431) of the frontal wall (201). While the secondary retention means (540) comprise a secondary fitting orifice (544) arranged in at least one of the reliefs (531) of the frontal covering wall (301) coinciding with the orifice of the primary fitting orifice (444) suitable for the user of fitting screws (109).

Although it is not shown in the present example, the same would apply if the position of the marks (421) and of the reliefs (521) is inverted.

Figure 9:
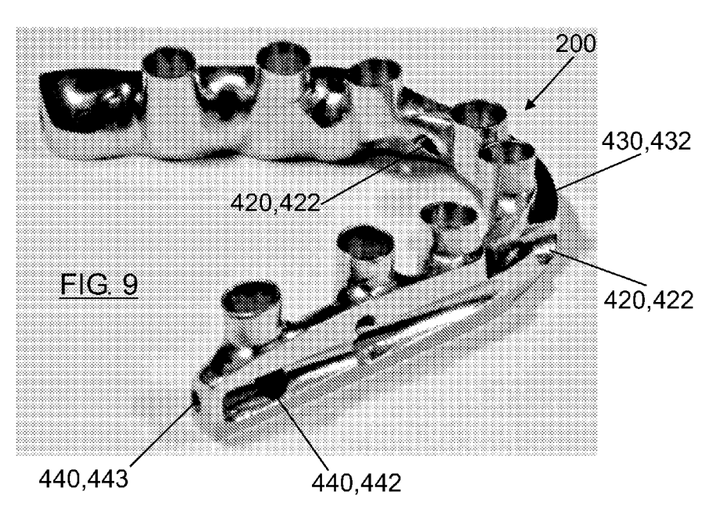
FIG. 9 is a perspective view of the lower part of the primary structure according to a second embodiment.
Figure 10:
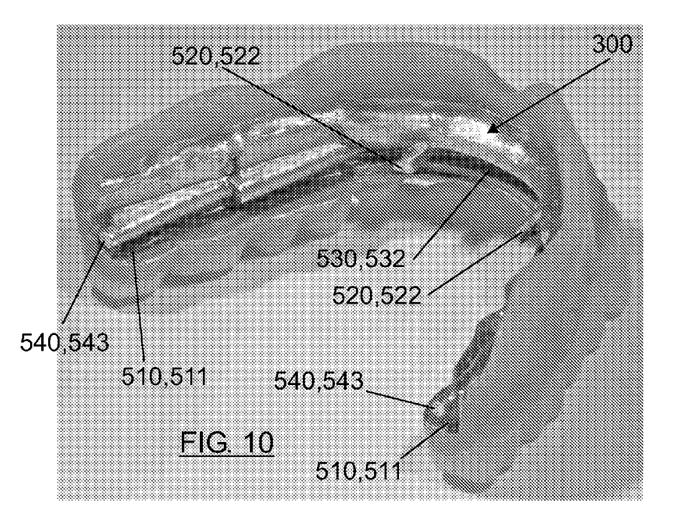
FIG. 10 is a perspective view of the lower part of the secondary structure together with the reproduction of the teeth and of the gum according to a second embodiment.

FIGS. 8, 9 and 10 show a second embodiment of the present invention, where it can be seen that the primary fitting means (430) comprise a rail-like front extension (432) from the upper part of the frontal wall (201); while the secondary fitting means (530) comprise a fastening notch (532) mechanized on the inner occlusal face of the frontal covering wall (301) formed to fit with the front extension (432) of the primary fitting means (430).

The perspective view of the upper part of the secondary structure according to the second embodiment has not been represented, as it coincides with the view of FIG. 5.

FIGS. 8, 9 and 10 also show how the primary (420) and secondary guiding means (520) can be complemented with guiding orifices (422) and orientation axes (522) which promote the functions thereof. Specifically, the guiding orifices (422) are arranged through the frontal wall (201), while the orientation axes (522) protrude from the inner face of the frontal covering wall (301) in a direction parallel to the guiding orifices (422), which in turn coincides with the direction of the vestibular insertion. In this way, very few millimeters into the complete insertion, the orientation axes (522) start to be inserted into the guiding orifices (422) preventing undesired deviations, and once they are completely inserted therein, counteracting axial and non-axial stress.

Figure 11:
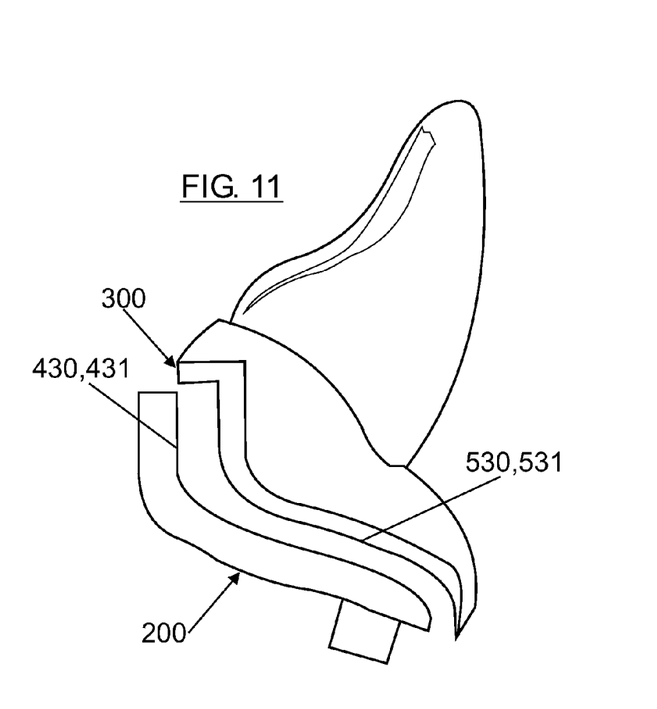
FIG. 11 is a schematic view of platform-type fit corresponding to the first embodiment.

FIG. 11 shows how the primary structure and the secondary structure interact according to the first preferred embodiment, that it, according to the "platform type".

Figure 12:
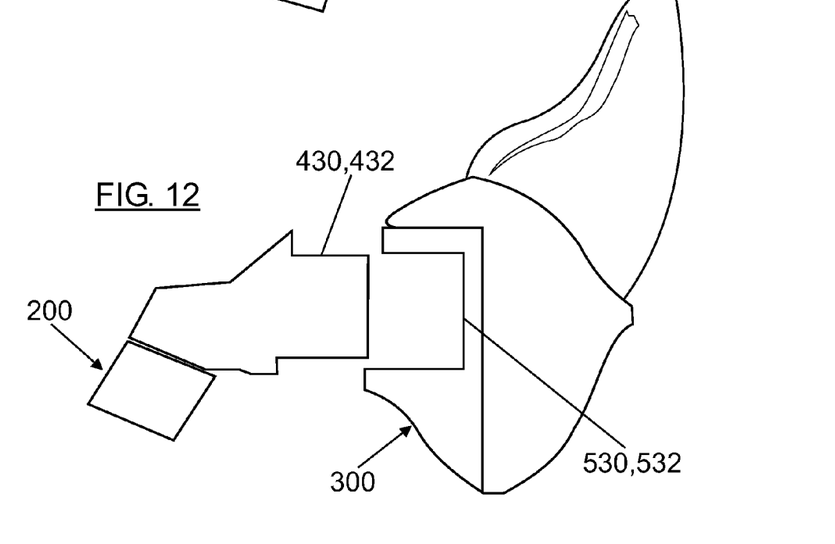
FIG. 12 is a schematic view of claw-type fit corresponding to the second embodiment.

FIG. 12 shows how the primary structure and the secondary structure interact according to the second preferred embodiment, that is, according to the "claw type".

The invention claimed is:

1. Dental prosthesis configured for fixing to a dental arch, completely or partially edentulous, said prosthesis comprising:
   a primary structure configured to be screwed on implants of the dental arch and includes:
      a primary insert; and
   a secondary structure configured to support a reproduction of the teeth and of the gum of the dental arch and includes:
      a secondary insert;
      wherein the primary insert and the secondary insert are configured to work in collaboration to enable coupling of the secondary structure on the primary structure through horizontal movement of one of the primary structure or the secondary structure relative to the other of the primary structure or the secondary structure.

2. The dental prosthesis according to claim 1, wherein the primary structure comprises:
   a frontal wall configured to occupy a frontal space, partially or totally, corresponding to the location incisors and canines of the dental arch; and
   at least one lateral wall joined to the frontal wall, the lateral wall being configured to occupy the lateral space, partially or totally, corresponding to the location of molars and premolars of one side of the dental arch.

3. The dental prosthesis according to claim 2, wherein each of the frontal wall and the lateral wall comprises at least a fixing pillar oriented to facilitate the fixing to the implants, the fixing pillar comprising:
   an end; and
   a through hole configured to receive a fixation screw to connect to an implant.

4. The dental prosthesis according to claim 2, wherein the secondary structure comprises:
   a frontal covering wall configured to fit with an outer face of the frontal wall and cover the frontal wall; and
   at least one lateral covering wall attached to the frontal covering wall formed to fit with the outer face of the lateral wall and cover the outer face of the lateral wall.

5. Dental prosthesis configured for fixing to a dental arch, completely or partially edentulous, said prosthesis comprising:
   a primary structure configured to be screwed on implants of the dental arch and includes:
      a primary insert;
      a frontal wall configured to occupy a frontal space, partially or totally, corresponding to the location incisors and canines of the dental arch; and
      at least one lateral wall joined to the frontal wall, the lateral wall being configured to occupy the lateral space, partially or totally, corresponding to the location of molars and premolars of one side of the dental arch; and
   a secondary structure configured to support a reproduction of the teeth and of the gum of the dental arch and includes:
      a secondary insert; wherein the primary insert and the secondary insert are configured to work in collaboration to enable coupling of the secondary structure on the primary structure through horizontal movement of one of the primary structure or the secondary structure relative to the other of the primary structure or the secondary structure;
      a frontal covering wall configured to fit with an outer face of the frontal wall and cover the frontal wall; and
      at least one lateral covering wall attached to the frontal covering wall formed to fit with the outer face of the lateral wall and cover the outer face of the lateral wall;
      wherein the frontal covering wall and the lateral covering wall comprise a plurality of protuberances configured to support the reproduction of the teeth and of the gum of the dental arch and facilitate formation of the dental arch.

6. The dental prosthesis according to claim 1, wherein the primary insert and the secondary insert respectively comprise a primary support and a secondary support allowing occlusal support of the secondary structure on the primary structure, wherein:
   the primary support comprises an external flat occlusal surface on the primary structure; and
   the secondary support comprises an internal flat occlusal surface on the secondary structure.

7. The dental prosthesis according to claim 1, wherein the primary insert and the secondary insert further comprise respectively a primary guide and a secondary guide configured to guide the secondary structure on the primary structure during the horizontal movement, wherein:
   the primary guide comprises a plurality of horizontal recesses or protrusions mechanized in a staggered manner along the outer face of the lateral wall; and
   the secondary guide comprises a plurality of horizontal protrusions or recesses mechanized along the inner face of the lateral covering wall configured to fit respectively with the horizontal recesses or protrusions of the primary guide and move along the horizontal recesses or protrusions until the secondary structure rests completely on the primary structure.

8. The dental prosthesis according to claim 1, wherein the primary insert and the secondary insert further comprise respectively a primary fitting and a secondary fitting configured to assemble the secondary structure with the primary structure during the horizontal movement.

9. Dental prosthesis configured for fixing to a dental arch, completely or partially edentulous, said prosthesis comprising:
   a primary structure configured to be screwed on implants of the dental arch and includes:
      a primary insert; and
   a secondary structure configured to support a reproduction of the teeth and of the gum of the dental arch and includes:
      a secondary insert;
      wherein the primary insert and the secondary insert are configured to work in collaboration to enable coupling of the secondary structure on the primary structure through horizontal movement of one of the primary structure or the secondary structure relative to the other of the primary structure or the secondary structure;
      wherein the primary insert and the secondary insert further comprise respectively a primary fitting and a secondary fitting configured to assemble the secondary structure with the primary structure during the horizontal movement;

the primary fitting comprising:
a rail-like front extension from the upper part of the frontal wall;

and the secondary fitting comprising:
a fastening notch mechanized on an inner occlusal face of the frontal covering wall formed to fit with the front extension of the primary fitting.

10. The dental prosthesis according to claim 1, wherein the primary insert and the secondary insert further comprise respectively a primary retainer and a secondary retainer configured to fix the secondary structure on the primary structure after the horizontal movement.

11. The dental prosthesis according to claim 2 further comprising a primary retainer and a secondary retainer, wherein the primary retainer and the secondary structure comprise a plurality of lateral orifices arranged respectively to be coincident on the lateral wall and on the lateral covering wall suitable for use of retention pins.

12. The dental prosthesis according to claim 6 further comprising a primary retainer and a secondary retainer, wherein the primary retainer and the secondary retainer comprise a plurality of axial orifices arranged respectively to be coincident on the outer occlusal surface on the primary structure and on the inner occlusal surface on the secondary structure suitable for the use of retention screws.

13. Dental prosthesis configured for fixing to a dental arch, completely or partially edentulous, said prosthesis comprising:

a primary structure configured to be screwed on implants of the dental arch and includes:
a primary insert; and
a secondary structure configured to support a reproduction of the teeth and of the gum of the dental arch and includes:
a secondary insert;
wherein the primary insert and the secondary insert are configured to work in collaboration to enable coupling of the secondary structure on the primary structure through horizontal movement of one of the primary structure or the secondary structure relative to the other of the primary structure or the secondary structure; and
wherein the primary insert and the secondary insert further comprise respectively a primary guide and a secondary guide configured to guide the secondary structure on the primary structure during the horizontal movement:

the primary guide comprising a plurality of horizontal recesses or protrusions mechanized in a staggered manner along the outer face of the lateral wall; and the secondary guide comprising a plurality of horizontal protrusions or recesses mechanized along the inner face of the lateral covering wall configured to fit respectively with the horizontal recesses or protrusions of the primary guide and move along the horizontal recesses or protrusions until the secondary structure rests completely on the primary structure;

a primary retainer and a secondary retainer, wherein the primary retainer comprises:
a primary end orifice arranged at an end of the horizontal recess or protrusion furthest from the frontal wall; and
wherein the secondary retainer comprises:
an axis arranged at an end of the horizontal protrusion or recess furthest from the frontal wall, wherein the frontal wall fits with the primary end orifice.

* * * * *